United States Patent [19]

Klaveness et al.

[11] Patent Number: 5,529,766
[45] Date of Patent: Jun. 25, 1996

[54] CONTRAST AGENTS

[75] Inventors: Jo Klaveness, Oslo; Pål Rongved, Nesoddtaugen; Per Strande, Oslo, all of Norway

[73] Assignee: Nycomed Imaging AS, Oslo, Norway

[21] Appl. No.: 119,218

[22] PCT Filed: Mar. 28, 1992

[86] PCT No.: PCT/EP92/00716

§ 371 Date: Oct. 29, 1993

§ 102(e) Date: Oct. 29, 1993

[87] PCT Pub. No.: WO92/17213

PCT Pub. Date: Oct. 15, 1992

[30] Foreign Application Priority Data

Mar. 28, 1991 [GB] United Kingdom ............... 9106686

[51] Int. Cl.$^6$ .................................................. A61K 49/00
[52] U.S. Cl. ........................................................ 424/9.52
[58] Field of Search .................. 424/9, 9.52; 128/662.02

[56] References Cited

U.S. PATENT DOCUMENTS 5,069,936 12/1991 Yen .............................. 427/213.33
5,271,928 12/1993 Schneider et al. .................. 424/9
5,310,540 5/1994 Giddey et al. ...................... 424/9

FOREIGN PATENT DOCUMENTS

| 0224934 | 6/1987 | European Pat. Off. . |
| 0441468 | 8/1991 | European Pat. Off. . |
| WO-A-9204392 | 3/1992 | WIPO . |

OTHER PUBLICATIONS

Bleeker et al., *The Journal of the Acoustical Society of America*, vol. 87, No. 4, Apr. 1990, pp. 1792–1797.
Baumert et al., *Methods in Enzymology*, vol. 172, part S, 1989, pp. 584–609.

*Primary Examiner*—Allen J. Robinson
*Assistant Examiner*—Mary C. Cebulak
*Attorney, Agent, or Firm*—Bacon & Thomas

[57] ABSTRACT

The invention relates to ultrasound contrast agents comprising vesicles comprising a protein capable of formation of gas-containing vesicles, wherein the vesicles contain gas which comprises sulphur hexafluoride or a low molecular weight fluorinated hydrocarbon. These contrast agents exhibit stability in vivo upon administration so as to permit ultrasound visualization while allowing rapid subsequent elimination from the system.

30 Claims, No Drawings

CONTRAST AGENTS

This application has been filed under 35 U.S.C. 371 from application PCT/EP92/00716.

This invention relates to novel contrast agents, more particularly to new gas-containing or gas-generating contrast agents of use in diagnostic ultrasonic imaging.

It is well known that ultrasonic imaging comprises a potentially valuable diagnostic tool, for example, in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas bubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of stabilising gas bubbles for echocardiography and other ultrasonic studies, for example using emulsifiers, oils, thickeners or sugars.

WO 80/02365 discloses the use of gelatin encapsulated gas microbubbles for enhancing ultrasonic images. Such microbubbles do not, however, exhibit adequate stability at the dimensions preferred for use in echocardiography (1–10 µm) in view of the extreme thinness of the encapsulating coating.

EP-A-0327490 discloses, inter alia, ultrasonic contrast agents comprising a microparticulate synthetic biodegradable polymer (e.g. a polyester of a hydroxy carbonic acid, a polyalkyl cyanoacrylate, a polyamino acid, a polyamide, a polyacrylated saccharide or a polyorthoester) containing a gas or volatile fluid (i.e. having a boiling point below 60° C.) in free or bonded form. Emulsifiers may be employed as stabilisers in the preparation of such agents, but such emulsifiers do not chemically interact with the polymer.

U.S. Pat. No. 4,774,958 discloses the use of microbubble dispersions stabilised by encapsulation in denatured protein, e.g. human serum albumin (HSA). Such systems permit the production of microbubble systems having a size of e.g. 2–5 µm but still do not permit efficient visualisation of the left heart and myocardium.

Other ultrasound contrast agents using proteins as encapsulating agents have been described in the literature, for example in EP 0359 246 (Molecular Biosystems), U.S. Pat. No. 4,832,941 (Max-Planck Gessellschaft), U.S. Pat. No. 4,844,882 (Molecular Biosystems), WO 84/02838 (Feinstein), U.S. Pat. No. 4,572,203 (Feinstein), EP 0077 752 (Schering), U.S. Pat. No. 4,747,610 (The Regents of the University of California), WO 80/02365 (Rasor), U.S. Pat. No. 4,774,958 (Feinstein), U.S. Pat. No. 4,718,433 (Feinstein), EP 0224 934 (Feinstein).

The only protein-based ultrasound contrast agent under commercial development consists of a suspension of gas-filled albumin, microbubbles Albunex®, prepared by sonication of a solution of albumin.

Albumin based ultrasound contrast agents are described in the following publications:

Feinstein et al. in Circulation 78S, 565 (1988), Reisner et al. in Circulation 78S, 565 (1988), Dick et al. in Circulation 78S, 565 (1988), Armstrong et al. in Circulation 78S, 565 (1988), Desir et al. in Circulation 78S, 566 (1988), Heidenreich et al. in Circulation 78S, 566 (1988), Keller et al. in Circulation 78S, 567 (1988), Barnhart et al. in Contrast Media Research (1989), Silverman et al. in Circulation 80S, 369 (1989), Silverman et al. in Circulation 80S, 349 (1989), Segar et al. in Clin. Res. 37, 294 (1989), Heidenreich et al. in Circulation 80S, 370 (1989), Reiser et al. in Circulation 80S, 370 (1989), Heidenreich et al. in Circulation 80S, 566 (1989), Shandas et al. in Circulation 82, 95 (1990), Geny et al. in Circulation 82, 95 (1990), Ten-Cate et al. in Eur Heart J. 19, 389 (1989), Feinstein et al. in Echocardiography 6, 27 (1989), Zotz et al. in Eur Heart J. 11, 261 (1990), Tencate et al. in Eur Heart J. 11, 261 (1990), Barnhart et al. in Invest Radiol 25S, 162 (1990), Keller et al. in J. Am Soc Echo 2, 48 (1989), Bleeker et al. in J. Acoust Soc Am 87, 1792 (1990), Feinstein et al. in J. Am. Coll. Cardiol 16, 316 (1990), Kaul et al. in J. Am Coll. Cardiol 15, 195 (1990), Bleeker et al in J. Ultrasound Med 9, 461 (1990), Hilpert et al. in Radiology 173, 361 (1989), and Shapiro et al. in J. Am. Coll. 16, 1603 (1990).

However, as indicated above, ultrasound contrast agents based on gas-filled protein microspheres (i.e., protein encapsulated gas microbubbles) are unstable in vivo, and there is room for improvement of such products. Segar et al. have, in Advances in Echocardiography (Sep. 21–22, 1989), concluded that batch, mixing pressure, mixing time and medium all affect the left atrium contrast with such protein based products.

Feinstein et al. have in J. Am. Coil. Cardiol 16, 316 (1990) published that irrespective of dose group, a cavity opacification with albumin microspheres was seen in the right ventricle in 88% of the injections and in the left ventricle in 63% of the injections. Shandas et al. have in Circulation 82, 95 (1990) raised questions about the pressure related stability of gas filled albumin microspheres and Shapiro et al. have recently published in J. Am. Coll. Cardiol 16, 1603 (1990) lack of ultrasound myocardial contrast enhancement after administration of sonicated albumin.

Feinstein has in EP 0224 934 on page 4,8 and claim 9, U.S. Pat. No. 4,718,433 columns 3 and 5 and U.S. Pat. No. 4,774,958 columns 3 and 5 suggested chemical denaturation to stabilize albumin gas bubbles:

"The microbubbles formed from 5% albumin may, in the alternative, be stabilized to form a commercially, clinically usable contrast agent by treatment with various chemical agents which chemically denature, or "fix", the protein, and derivatives thereof. Chemical denaturation of the protein (or derivatives) may be accomplished by either binding the protein with a protein-reactive aldehyde, such as glutaraldehyde. For the latter procedure of stabilizing the invented microbubble contrast agent, the microbubbles may be reacted with 0.25 grams of 50% aqueous glutaraldehyde per gram of protein at pH 4.5 for 6 hours. The treated contrast agent is then gently and extensively washed to remove as much of the unreacted glutaraldehyde as possible."

Various denaturing chemicals or crosslinking agents for proteins have been described in the literature. (See for example Methods Enzymol 172, 584 (1989) and Chemical Reagents for Protein Modification, Volume II, page 123, CRC Press Inc.)

However it is important that any contrast agent should be rapidly eliminated from the subject in a short term after use, e.g. preferably having a half life of not more than 48 hours.

Crosslinking by glutaraldehyde or formaldehyde may not always be effective in providing an adequate balance between stability during ultrasound visualisation and rapid elimination. The protein itself, being human serum albumin, is not rapidly degraded by vascular enzymes and reagents such as glutaraldehyde do not form readily biodegradable bonds with the protein.

The present invention is based on the concept of crosslinking the protein shells of microbubbles to introduce biodegradable linking groups, thus providing ultrasound contrast agents with adequate stability for the duration of ultrasound visualisation but sufficient biodegradability to permit rapid elimination subsequently.

According to the present invention, therefore, we provide ultrasound contrast agents comprising microbubbles of gas or a gas precursor encapsulated in a shell of protein crosslinked with biodegradable crosslinking groupings.

Biodegradable linkages which may be used include amide, imide, imine, ester, anhydride, acetal, carbamate, carbonate, carbonate ester and disulphide groups. At least one such group should preferably be present in the crosslinking grouping. In general, any esters will be biodegradable particularly those containing the grouping —CO.O— or —O.CO.O—. One particularly useful class of biodegradable ester groupings has the structure $$-(Y)_n.CO.O.C(R^1R^2).O.CO.(Z)_n-$$

(where Y and Z, which may be the same or different, are —O—, —S— or —NR$^3$—; the symbols n, which may be the same or different, are zero or 1; R$^1$ and R$^2$, which may be the same or different, are hydrogen atoms or carbon-attached monovalent groups or together represent a carbon-attached divalent organic group; and R$^3$ is a hydrogen atom or an organic group. Y and Z are preferably —O—. Such groups generally degrade to eliminate a compound R$^1$R$^2$CO and either form carboxyl groups on the residue or, in the case of carbonate esters, may eliminate carbon dioxide to form hydroxyl groups on the residue.

R$^1$, R$^2$ and R$^3$ may each be a hydrocarbyl or heterocyclic group, for example having 1–20 carbon atom, e.g. an alkyl or alkenyl group (preferably having up to 10 carbon atoms), a cycloalkyl group (preferably having up to 10 carbon atoms), an aralkyl group (preferably having up to 20 carbon atoms), an acyl group (preferably having up to 20 carbon atoms) or a heterocyclic group having up to 20 carbon atoms and one or more heteroatoms selected from O, S and N; such a hydrocarbyl or heterocyclic grouping may carry one or more functional groups such as halogen atoms or groups of the formulae —NR$^4$R$^5$, —CONR$^4$R$^5$, —OR$^6$, —SR$^6$ and —COOR$^7$, where R$^4$ and R$^5$, which may be the same or different, are hydrogen atoms, acyl groups or hydrocarbyl groups as defined for R$^1$ and R$^2$; R$^6$ is a hydrogen atom or an acyl group or a group as defined for R$^1$ or R$^2$ and R$^7$ is a hydrogen atom or a group as defined for R$^1$ or R$^2$; where R$^1$ and R$^2$ represent a divalent grouping, this may for example be an alkylene or alkenylene group (preferably having up to 10 carbon atoms) which may carry one or more functional groups as defined above. In general R$^1$ and R$^2$ are preferably hydrogen or small groups such as C$_{1-4}$ alkyl groups.

The protein component can be any protein or derivative thereof including polyamino acids. Albumin, gelatin and δ-globulin are representative compounds. The protein, for instance albumin, can be obtained from biological sources, for example from human or animal blood, or produced by a lower organism using recombinant technology. A typical method for preparation of human serum albumin by fermentation is described in WO 9002808 (Delta Biotechnology Ltd.).

According to a further feature of the invention, we provide a process for the preparation of microbubble ultrasound contrast agents in which a gas or a gas precursor is encapsulated in a protein which is crosslinked with biodegradable crosslinking groups.

The crosslinking of the protein can be effected before, during or after encapsulation. It is preferred to encapsulate, e.g. by forming microbubbles, first and to effect crosslinking subsequently.

The crosslinking agent may be a compound of the formula (I)

$$A^1-X-A^2 \qquad (I)$$

where X is a linking group containing one or more biodegradable linkages and the groups A$^1$ and A$^2$, which may be the same or different, are functional groups reactive with proteins.

The group X may carry further groups reactive with proteins to provide an even greater degree of crosslinking.

Preferably, the group X should have a chain length of not more than 30 atoms.

The group X may thus be of the form $$-R^8-E-R^9-$$

where R$^8$ and R$^9$, which may be the same or different, are divalent organic groups, for example alkylene or alkylidene groups having 1–12 carbon atoms, which may carry groups reactive with proteins and/or further inert groups, and the group E is an ester grouping, for example of the formula —O.CO—, —O.CO.O— or —(Y)$_n$.CO.O.C(R$^1$R$^2$).O.CO.(Z)$_n$— as defined above.

Crosslinking agents of the formula $$A^1.R^8.(Y)_n.CO.O.C(R^1R^2).O.CO.(Z)_n.R^9.A^2$$

where A$^1$, A$^2$, R$^1$, R$^2$, R$^8$, R$^9$, n, Y and Z have the above meanings may be prepared by reaction of an acid of the formula A$^1$.R$^8$.(Y)$_n$.CO.OH or a form thereof in which A$^1$ and any other reactive groups are protected (or a functional derivative thereof) with a compound of the formula L$^1$.C(R$^1$R$^2$).L$^2$ where L$^1$ is a leaving group such as a halogen atom or mesyloxy or tosyloxy and L$^2$ is a group as defined for L$^1$ (giving a symmetrical di-ester) or a group of the formula —O.CO.(Z)$_n$.R$^9$.A$^2$ or a protected form thereof, if necessary followed by deprotection. The functional derivative of the acid may for example be a salt, e.g. the potassium salt. The reaction will normally be carried out in solution, for example in a polar solvent such as dimethylformamide. Protecting groups for A$^1$ and A$^2$ may be those conventional in the art. Preferred protecting groups for aldehydes include acetals, e.g. cyclic acetals such as dioxolan.

The compound L$^1$.C(R$^1$R$^2$).O.CO.(Z)$_n$.R$^9$.A$^2$, where L$^1$ is halogen, may be prepared from R$^1$R$^2$.CO by reaction with a compound of the formula Hal.CO.(Z)$_n$.R$^9$.A$^2$ (where Hal represents a halogen atom) in the presence of a base such as pyridine.

Apart from aldehyde groups, which are preferred, the groups A$^1$ and A$^2$ may be activated carboxyl groups, such as N-hydroxysuccinimidyl groups (especially water solubility-enhanced sulphonated N-hydroxysuccinimidyl derivatives), imidoesters, halo-nitroaryl groups, nitrene precursor groups such as azidophenyl, carbene precursor groups, ketone groups, isothiocyanate groups etc.

Any biocompatible gas may be employed in the contrast agents of the invention, for example air, nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The gas may be free within the microbubble or may be trapped or entrained within a containing substance. The term "gas" as used herein includes any substance in the gaseous form at 37° C.

Gas precursors include carbonates and bicarbonates, e.g. sodium or ammonium bicarbonate and aminomalonate esters.

For applications in echocardiography, in order to permit free passage through the pulmonary system and to achieve resonance with the preferred imaging frequency of about 0.1–15 MHz, it may be convenient to employ microbubbles having an average size of 0.1–10 µm, e.g. 1–7 µm. Substantially larger bubbles, e.g. with average sizes of up to 500 µm, may however be useful in other applications, for example gastrointestinal imaging or investigations of the uterus or Fallopian tubes.

As indicated above the microbubbles may be stabilised by incorporation of particulate material together with the encapsulated gas. Such particles include, for example, silica and iron oxide. The preferred particle size for such stabilising particles is in the range 1 to 500 nm, depending on the size of the microbubbles. The particles should be such that they are only partially wetted by the fluid medium used to disperse the micelles, i.e. the contact angle between the material of the particles and the fluid should be about 90 degrees.

The stabilising particles may carry functional groups which will interact with the protein to form covalent or other linkages. Colloidal silica particles may have a particle size in the range 5–50 nm and may carry silanol groups on the surface which are capable of interaction with the protein by hydrogen bonding or by forming covalent bond.

The protein may stabilize the gas or gas precursor by forming a monolayer at the interface between the liquid medium and the gas or gas precursor system, or by forming vesicles consisting of one or more bilayers containing the gas or gas precursor.

The stabilisation of the system by monolayers or the formation of the vesicles may be activated, as fully described in the literature, by sonication or even shaking of the protein material mixture in the appropriate medium, or the vesicles may be formed by any conventional liposome/vesicle-forming principle.

The stabilized microbubbles may be dried or freeze-dried or the non-aqueous phase may be evaporated. The resulting dried system may be resuspended in any physiological acceptable solvent such a saline or phosphate buffer, optionally using a suspending or emulsifying agent.

A gas entrapped system may be obtained by using a gas precursor or the gas itself may be entrapped. The gas may be entrapped into the amphiphile mixture simply by vigorously shaking the mixture in the presence of air, i.e. creating a gas-in-liquid emulsion as described in U.S. Pat. No. 4,684,479. Another well established method, described i.e. in U.S. Pat. No. 4,774,958 for creating a gas-containing bubble is by sonication of the mixture in the presence of air. Another well known method is passing the gas through a syringe into the mixture of the protein and the liquid. As described in U.S. Pat. No. 3,900,420 the microgas-emulsion may be created by using an apparatus for introducing gas rapidly into a fast-flowing liquid. A region of low pressure is created in a liquid containing the protein material. The gas is then introduced to the region of low pressure and the gas-in-liquid system is obtained by pumping the liquid through the system.

By using the principle of electrolysis it is possible to generate the gas to be entrapped directly in a container containing the protein material. The electrolytes necessary for the electrolysis may even help to further stabilize the protein material. An aqueous solution containing electrolytes may generate hydrogen gas at the cathode and oxygen at the anode. The electrodes may be separated by a salt bridge. On adding hydrazine nitrogen gas may be generated at the anode. Using the Kolbe reaction, one may also generate $CO_2$ from carboxylic acids using electrolysis.

As described above, microbubbles may be obtained by forming liposomes or vesicles consisting of one or more bilayers. These vesicles may be formed at elevated pressure conditions in such a way that the gas is entrapped in the vesicles.

In one procedure according to the invention, encapsulation is effected by agitation or sonication of the protein in an aqueous medium to yield a protein foam which is dried and thereafter suspended in a solution of the crosslinking agent in a polar organic solvent (e.g. a sulphoxide such as dimethyl sulphoxide) which is capable of wetting the protein foam.

The following Examples are given by way of illustration only:

PREPARATION 1

Methylene Bis (α-Formylacetate)

The preparation of the starting material, the dioxolan-protected aldehyde methyl α-formylacetate, is described by T. Hosokawa et al. J. Org. Chem. Soc. 52, (1987) 1758–1764. The protected aldehyde (6.0 g, 3.75 mmol) is treated with a mixture of 2N aqueous potassium hydroxide and tetrahydrofuran 20:80 (v/v) at reflux for 8 hours. The pH is adjusted to 8 using diluted HCl, and the mixture is evaporated to dryness. The solid is mixed with 100 ml freshly distilled and dried dimethylformamide, and after 30 minutes at 60° C. the undissolved material is filtered off. Diiodomethane (150 µl, 1.87 mmol) is added dropwise during 5 minutes to the solution at 60° C. as described in WO 89/00988 page 13 (NYCOMED AS). The precipitate is removed by filtration after stirring for 4 days, and the solvent removed at reduced pressure. The dioxolan protection is removed as described by P. A. Grieco et al. J. Am. Chem. Soc. 99, (1977) 5773–5780—the residue is dissolved in tetrahydrofuran (60 ml), 5% aqueous HCl (20 ml) is added and the mixture is stirred for 20 hours at ambient temperature. The reaction mixture is evaporated to dryness under reduced pressure to yield the title compound.

PREPARATION 2

Methylene Dimethacrylate

A solution of potassium hydroxide (1.00M, 40.00 ml) is added to methacrylic acid (3.44 g, 40.00 mmol) at 0° C. and the solution freeze dried for 16 hours. Dry dimethylformamide (230 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried. ($MgSO_4$), and evaporated to give 2.63 g (72%) of the title compound. $^1H$ NMR (60 MHz, $CDCl_3$): δ 1.97 (2×$CH_3$, m), 5.63 (2×H—C=, m), 5.88 (CH$_2$, s), 6.18 (2×H—C=, m). IR (film, cm$^{-1}$): 2987 (w), 2962 (w), 2930 (w), 1732 (str), 1638 (w), 1454 (w), 1315 (w), 1295 (w), 1158 (w), 1100 (str), 1012 (m), 989 (m). This product may be used in accordance with the invention, for example to crosslink acrylamide polymers.

PREPARATION 3

Methylene Diacrylate

A solution of potassium hydroxide (1.00M, 40.00 ml) is added to acrylic acid (2.88 g, 40.00 mmol) at 0° C. and the solution freeze dried for 16 hours. Dry dimethylformamide (200 ml) is added and the suspension heated to 60° C. under a dry nitrogen atmosphere. Diiodomethane (1.61 ml, 20.00 mmol) is added in two portions during 10 min. and the reaction mixture left for 4 days at 60° C. The solvent is removed under reduced pressure (0.05 mm Hg), before diethyl ether (140 ml), saturated aqueous sodium hydrogen carbonate (50 ml) and water (50 ml) are added. The aqueous layer is extracted with diethyl ether (6×60 ml) and the combined ether extracts washed with water (4×50 ml), dried (MgSO$_4$), and evaporated to give 1.06 g (34%) of the title compound. $^1$H NMR (60 MHz, CDCl$_3$): δ 5.81–6.61 (2×CH$_2$=CH—, m), 5.84 (CH$_2$, s). This product may be used in accordance with the invention, for example to crosslink acrylic acid and methyl acrylate polymers.

PREPARATION 4

Chloromethyl (2-Methacryloyloxy)ethyl Carbonate

Pyridine (0.89 ml, 11.00 mmol) is added dropwise to a solution of chloromethyl chloroformate (0.89 ml, 11.00 mmol) and 2-hydroxyethyl methacrylate (1.22 ml, 10.00 mmol) in dichloromethane (12 ml) at 0° C. under a dry nitrogen atmosphere. After 21 hours at 20° C. the reaction mixture is washed with hydrochloric acid (1.00 M, 10 ml), saturated aqueous sodium hydrogen carbonate (10 ml) and water (10 ml). The organic phase is dried (MgSO$_4$) and the solvent evaporated under reduced pressure (10 mm Hg) to give 1.97 g (88%) of the title compound. $^1$H NMR (60 MHz, CDCl$_3$): δ 1.88 (CH$_3$, d, J=2 Hz), 4.35 (O—CH$_2$—CH$_2$—O, m), 5.47 (H—C=, m), 5.63 (CH$_2$—Cl, s), 6.00 (H—C=, m).

PREPARATION 5

(2-Methacryloyloxy)ethyl Methacryloyloxymethyl Carbonate

A solution of potassium hydroxide (1.00M, 5.00 ml) is added to methacrylic acid (0.43 g, 5.00 mmol) at 0° C. and the solution freeze dried during 16 hours. Dry dimethylformamide (50 ml) is added and to the resulting suspension is added chloromethyl (2-methacryloyloxy) ethyl carbonate (1.11 g, 5.00 mmol). 18-Crown-6 (0.066 g, 0.25 mmol) is added as a catalyst and the reaction left under a dry nitrogen atmosphere. After 24 hours at 20° C. and 6 days at 4° C. the solvent is removed under reduced pressure (0.05 mm Hg) and diethyl ether (30 ml) and water (20 ml) added. The aqueous layer is extracted with diethyl ether (3×20 ml) and the combined ether extracts washed with water (20 ml), dried (MgSO$_4$) and evaporated to give 1.26 g (93%) of the title compound. $^1$H NMR (60 MHz, CDCl$_3$): δ 1.97 (2×CH$_3$, m), 4.38 (O—CH$_2$—CH$_2$—O, m), 5.53 (2×H—C=, m), 5.77 (CH$_2$, s), 6.07 (2×H—C=, m).

PREPARATION 6

Ethylene Bis(chloromethyl Carbonate)

Pyridine (0.89 ml, 11.00 mmol) is added dropwise to a solution of chloromethyl chloroformate (1.32 ml, 14.83 mmol) and ethylene glycol (0.28 ml, 5.00 mmol) in dichloromethane (10 ml) at 7° C. with good stirring under a dry N$_2$ atmosphere. After 15 min. at 7° C. and 6 hours at 20° C. the reaction mixture is transferred to a separating funnel with the aid of dichloromethane (10 ml). The reaction mixture is washed with hydrochloric acid (1.00 M, 10 ml), saturated aqueous sodium hydrogen carbonate (10 ml) and water (10 ml). The organic phase is dried (MgSO$_4$) and the solvent evaporated under reduced pressure to give 1.12 g (90%) of the title product. $^1$H NMR (300 MHz, CDCl$_3$): δ 4.48 (s, O—CH$_2$CH$_2$—O), 5.75 (s, 2×Cl—CH$_2$—O). $^{13}$C NMR (75 MHz, CDCl$_3$): δ 65.8 (O—CH$_2$CH$_2$—O), 72.2 (2 ×Cl—CH$_2$—O), 153.0 (2×C=O).

PREPARATION 7

Bis(2-chloromethoxycarbonyloxyethyl)ether

Pyridine (0.89 ml, 11.00 mmol) is added dropwise to a solution of chloromethyl chloroformate (1.32 ml, 14.83 mmol) and diethylene glycol (0.47 ml, 5.00 mmol) in dichloromethane (10 ml) at 7° C. with good stirring under a dry N$_2$ atmosphere. After 10 min. at 7° C. and 6 hours at 20° C. the reaction mixture is transferred to a separating funnel with the aid of dichloromethane (10 ml). The reaction mixture is washed with hydrochloric acid (1.00 M, 10 ml), saturated aqueous sodium hydrogen carbonate (10 ml) and water (10 ml). The organic phase is dried (MgSO$_4$) and the solvent evaporated under reduced pressure (10 mm Hg) to give 1.26 g (86%) title product. $^1$H NMR (300 MHz, CDCl$_3$): δ 3.72 (m, 2×CH$_2$—O), 4.34 (m, 2×CH$_2$—O—C=O), 5.71 (s, 2×Cl—CH$_2$—O). $^{13}$C NMR (75 MHz, CDCl$_3$): δ 67.6 (2×CH$_2$—O), 68.5 (2×CH$_2$—O—C=O), 72.1 (2 ×Cl—CH$_2$—O), 153.2 (2×C=O).

PREPARATION 8

1-Chloroethyl 2-Methacryloyloxyethyl Carbonate

Pyridine (0.89 ml, 11.00 mmol) is added dropwise to a solution of 1-chloroethyl chloroformate (1.20 ml, 11.00 mmol) and 2-hydroxyethyl methacrylate (1.22 ml, 10.00 mmol) in dichloromethane (12 ml) at 3° C. under a dry N$_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00 M, 10 ml), saturated aqueous sodium hydrogen carbonate (10 ml) and water (2×10 ml). The organic phase is dried (MgSO$_4$) and the solvent evaporated under reduced pressure to give 1.76 g (74%) of the title product. $^1$H NMR (60 MHz, CDCl$_3$): δ 1.85 (3 H, d, J=6 Hz, CH$_3$—CH), 1.96 (3 H,d, J=2 Hz, CH$_3$—C=), 5.55 (1 H, m, CH=), 6.10 (1 H, m, CH=), 6.38 (1 H, k, J=6 Hz, CH—CH$_3$).

PREPARATION 9

Chloromethyl 4-Acryloyloxybutyl Carbonate

Pyridine (0.89 ml, 11.00 mmol) is added dropwise to a solution of chloromethyl chloroformate (0.98 ml, 11.00 mmol) and 4-hydroxybutyl acrylate (1.38 ml, 10.00 mmol)

in dichloromethane (12 ml) at 3° C. under a dry $N_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00 M, 10 ml), saturated aqueous sodium hydrogen carbonate (10 ml) and water (2×10 ml). The organic phase is dried ($MgSO_4$) and the solvent evaporated under reduced pressure to give 1.76 g (74%) of the title product. $^1$H NMR (60 MHz, $CDCl_3$): δ 1.82 (4 H, m, $CH_2$—$CH_2$), 4.27 (4 H, m, 2×$CH_2$—O), 5.77 (2 H, s, Cl—$CH_2$—O), 5.8–6.7 (3 H, m, CH=$CH_2$).

PREPARATION 10

1-Chloroethyl 4-Acryloyloxybutyl Carbonate

Pyridine (0.89 ml, 11.00 mmol) is added dropwise to a solution of 1-chloroethyl chloroformate (1.20 ml, 11.00 mmol) and 4-hydroxybutyl acrylate (1.38 ml, 10.00 mmol) in dichloromethane (12 ml) at 3° C. under a dry $N_2$ atmosphere. After 15 min. at 3° C. and 17 hours at 20° C. the reaction mixture is transferred to a separating funnel with the aid of dichloromethane (10 ml). The reaction mixture is washed with hydrochloric acid (1.00 M, 10 ml), saturated aqueous sodium hydrogen carbonate (10 ml) and water (2×10 ml). The organic phase is dried ($MgSO_4$) and the solvent evaporated under reduced pressure to give 2.26 g (90%) of the title product. $^1$H NMR (60 MHz, $CDCl_3$): δ 1.80 (4 H, m, $CH_2$—$CH_2$), 1.86 (3 H, d, J=5 Hz, $CH_3$), 4.24 (4 H, m, 2×$CH_2$—O), 5.7–6.6 (4 H, m, CH=$CH_2$ and CH).

PREPARATION 11

1-Methacryloyloxyethyl 2-Methacryloyloxyethyl Carbonate

1-Chloroethyl 2-methacryloyloxyethyl carbonate (1.183 g, 5.00 mmol) prepared as described in Preparation 8 is added to a suspension of freeze dried potassium methacrylate (0.683 g, 5.50 mmol) and 18-crown-6 (0.066 g, 0.25. mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.10 g (77%) of the title product. $^1$H NMR (60 MHz, $CDCl_3$): δ 1.63 (3 H, d, J=5 Hz, $CH_3$—CH), 1.98 (6 H, s, 2 ×$CH_3$), 4.42 (4 H, s, O—$CH_2$—$CH_2$—O), 5.62 (2 H, m, CH=), 6.15 (2 H, m, CH=), 6.84 (1 H, k, J=5 Hz, $CH$—$CH_3$).

PREPARATION 12

Acryloyloxymethyl 4-Acryloyloxybutyl Carbonate

Chloromethyl 4-acryloyloxybutyl carbonate (1.183 g, 5.00 mmol) prepared as described in Preparation 9 is added to a suspension of freeze dried potassium acrylate (0.606 g, 5.50 mmol) and 18-crown-6 (0.066 g, 0.25 mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.24 g (91%) of the title product. $^1$H NMR (60 MHz, $CDCl_3$): δ 1.82 (4 H, m, $CH_2$—$CH_2$), 4.23 (4 H, m, 2×$CH_2$—O), 5.88 (2 H, s, O—$CH_2$—O), 5.7–6.8 (6 H, 2×CH=$CH_2$).

PREPARATION 13

1-Acryloyloxyethyl 4-Acryloyloxybutyl Carbonate

1-Chloroethyl 4-acryloyloxybutyl carbonate (1.253 g, 5.00 mmol) prepared as described in Preparation 10 is added to a suspension of freeze dried potassium acrylate (0.606 g, 5.50 mmol) and 18-crown-6 (0.066 g, 0.25 mmol) in dimethylformamide (50 ml) under a dry $N_2$ atmosphere. After 5 days at 20° C. the solvent is removed under reduced pressure and the residue dissolved by adding dichloromethane (60 ml) and water (30 ml). After separating the phases the aqueous layer is extracted with dichloromethane (3×30 ml) and the combined organic phase washed with saturated aqueous sodium hydrogen carbonate (50 ml). The organic phase is dried ($MgSO_4$) and the solvent removed under reduced pressure to give 1.28 g (89%) of the title product. $^1$H NMR (60 MHz, $CDCl_3$): δ 1.58 (3 H, d, J=5 Hz, C$H_3$—CH), 1.80 (4 H, m, $CH_2$—$CH_2$), 4.24 (4 H, m, 2×$CH_2$—O), 5.7–6.7 (6 H, m, 2×CH=$CH_2$), 6.87 (1 H, k, J=5 Hz, C$H$—$CH_3$).

PREPARATION 14 a) Methylene bis(3,3-dimethoxypropionate)

Cesium 3,3-dimethoxypropionate (19.95 g, 75 mmol) is added to dry DMF (1000 ml). Diiodomethane (10.04 g, 37.5 mmol) is added to the suspension and the reaction mixture is stirred for 2 days at 60° C. under a dry $N_2$ atmosphere. DMF is removed under reduced pressure (0.01 mmHg). Diethyl ether (500 ml) is added to the residue, which is then washed with saturated aqueous sodium hydrogen carbonate (250 ml). The aqueous layer is extracted with diethyl ether (5×75 ml). The combined ether extracts are washed with water (2×100 ml), dried ($MgSO_4$) and evaporated to give 7.1 g (72%) product. $^1$H NMR (300 MHz, $CDCl_3$): δ 2.61 ($CH_2$, d), 3.26 ($CH_3$, s)

b) Methylene bis(3-methoxypropenoate)

Methylene bis(3,3-dimethoxypropionate) (14.01 g, 50 mmol) prepared as described in (a) above and a catalytic amount of p-toluene sulfonic acid is added to toluene (250 ml). The methanol is removed by warming the reaction under an $N_2$ atmosphere. When the reaction is complete the toluene is distilled off under reduced pressure. Diethyl ether (250 ml) is added and the mixture is washed with saturated aqueous sodium hydrogen carbonate (5×50 ml) and water (3×50 ml). The organic layer is dried ($MgSO_4$) before evaporation to give 8.52 g (79%) product. $^1$H NMR (300 MHz, $CDCl_3$): δ 3.65 (2×$CH_3$, s), 5.2 (2×CH, d), 5.8 (O—$CH_2$—O), 7.65 (2×$CH_2$, d).

PREPARATION 15 a) Methylene bis (10-undecenoate)

10-Undecylenic acid (12.75 g, 75 mmol) is dissolved in 100 ml water. Cesium carbonate (13.04 g, 40 mmol) is added to the mixture. The water is removed under reduced pressure and the salt dried for 2 hours in vacuo. The cesium salt is mixed with 150 ml DMF and diiodomethane is added to the solution. The reaction is stirred for 3 days at 60° C. under an $N_2$ atmosphere. DMF is then removed under reduced pressure. The residue is purified through silica gel with hexane/ethyl acetate (8:2) as eluant. The solvent is evaporated to give 7.18 g (54%) product. $^1$H NMR (300 MHz, CDCl$_3$): δ 1.2–1.4 (10 ×CH$_2$, m), 1.6 (2×CH$_2$, m), 2.0 (2×CH$_2$, m), 2.19 (2×CH$_2$, t), 4.9 (2×H$_2$ C=, m), 5.88 (O—CH$_2$—O, s), 5.9 (2×HC=, m). $^{13}$C NMR (300 MHz, CDCl$_3$): δ 24.92–33.98 (8×CH$_2$), 79.04 (O—CH$_2$—O), 114.18 (=CH$_2$), 139.11 (=CH), 172.48 (C=O).

b) Methylene bis(10-epoxyundecanoate)

Methylene bis(10-undecenoate) (8.8 g, 25 mmol) prepared as described in (a) above is added under an N$_2$ atmosphere to methylene chloride and cooled to 0° C. Metachloroperbenzoic acid 55% (15.75 g, 50 mmol) is added to methylene chloride (150 ml) and the organic layer is separated and dried (MgSO$_4$). The metachloroperbenzoic acid is then added dropwise to the diester. After completed addition the temperature is increased to 25° C. After 5 hours the reaction is complete. The mixture is washed with saturated aqueous sodium sulphite (75 ml) and saturated aqueous sodium hydrogen carbonate (2×75 ml). The organic layer is purified on neutral aluminium oxide. The solvent is removed under reduced pressure to yield 8.45 g (82%) product. $^1$H NMR (300 MHz, CDCl$_3$): δ 1.2–1.7 (14×CH$_2$, m), 2.35 (2×CH$_2$CO,t), 2.45 (2×CH, q), 2.75 (2×CH,q), 2.90 (2×CH,m), 5.75 (O—CH$_2$—O). $^{13}$C NMR (300 MHz, CDCl$_3$): δ 24.58 (CH$_2$), 25.99 (CH$_2$), 28.94 (CH$_2$), 29.09 (CH$_2$), 29.32 (2×CH$_2$), 32.45 (CH$_2$), 33.92 (CH$_2$), 47.06 (CH$_2$—O), 52.36 (CH—O), 79.06 (O—CH$_2$—O), 172.2 (C=O).

PREPARATION 16

Methylene Bis(4-epoxypentanoate)

Metachloroperbenzoic acid (15.68 g, 55%, 50 mmol) is dissolved in methylene chloride (200 ml). Water is separated and the organic layer is dried (MgSO$_4$). The resulting metachloroperbenzoic acid solution is added dropwise to methylene bis(4-pentenoate) (4.10 g, 19 mmol) dissolved in methylene chloride (50 ml). The mixture is stirred at ambient temperature under nitrogen for 12 hrs, whereafter the reaction mixture is washed with saturated aqueous sodium bicarbonate solution (50 ml), water (50 ml), dried (MgSO$_4$) and evaporated to give 3.61 g (78%) of the title compound as a crystalline product. $^1$H NMR (300 MHz, CDCl$_3$): δ 1.70–1.85 (2×CH,m), 1.95–2.10 (2×CH,m), 2.50–2.55 (2×CH, 2×CH$_2$,m), 2.75 (2×CH,t), 3.0 (2×CH,m), 5.8 (O—CH$_2$—O, s). $^{13}$C NMR (75 MHz, CDCl$_3$): δ 27 (2×CH$_2$), 30 (2×CH$_2$), 47 (2×CH$_2$), 51 (2×CH), 79.8 (O—CH$_2$—O), 171.8 (2×C=O).

PREPARATION 17

Methylene Bis(2-butenoate)

Vinylacetic acid (4.3 g, 50 mmol) is added to an aqueous cesium carbonate solution (50 ml). The mixture is stirred for 5 min. and then evaporated, and the residue is dried under vacuum for 2 hrs. The resulting cesium salt and diiodomethane are added to dimethylformamide (200 ml) and the mixture is stirred for 24 hrs. at 50° C. under nitrogen, whereafter the dimethylformamide is removed under reduced pressure. The residue is dissolved in diethyl ether (100 ml) and washed with saturated aqueous sodium bicarbonate (25 ml) and water (25 ml). The organic layer is dried (MgSO$_4$) and evaporated to give 1.32 g (29%) product. $^1$H NMR (300 MHz, CDCl$_3$): δ 1.9 (2×CH$_2$,m), 5.8–5.9 (2×CH, m), 5.9 (OCH$_2$O,s), 7.0–7.1 (2×CH,m).

PREPARATION 18

Methylene Bis(chloroacetate)

Chloroacetic anhydride (12.75 g, 75 mmol), paraformaldehyde (2.25 g, 75 mmol) and conc. sulfuric acid (15 drops) are added to methylene chloride (15 ml). The mixture is stirred for 24 hrs. at 50° C. under nitrogen, whereafter the reaction mixture is extracted with saturated aqueous potassium carbonate until carbon dioxide emission ends. The organic layer is dried (MgSO$_4$), evaporated to dryness and the residue is distilled (80° C., 0.15 mmHg) to yield 10.2 g (57%) product. $^1$H NMR (200 MHz, CDCl$_3$): δ 4.1 (2×CH$_2$Cl,s), 5.9 (CH$_2$,s). $^{13}$C NMR (200 MHz, CDCl$_3$): δ 41.1 (CH$_2$Cl), 81.4 (O—CH$_2$—O), 166.4 (CO).

PREPARATION 19

Methylene Bis(4-oxopentanoate)

4-Oxopentanoic acid (11.6 g, 100 mmol) is dissolved in acetonitrile (70 ml), and 1,8-diazabicyclo[5.4.0]undec-7-ene (15.25 g, 100 mmol) diluted with acetonitrile (30 ml) is added. Diiodomethane (13.4 g, 50 mmol) is added in one batch, and the reaction mixture is refluxed under a nitrogen atmosphere. After 2 hours, gas chromatography indicates full consumption of diiodomethane. The solvent is removed in vacuo and the residual brown oil is transferred to a separation funnel with ethyl acetate (200 ml) and water (75 ml). The organic phase is washed with 1M sodium bicarbonate (25 ml) and water (3×25 ml), dried over MgSO$_4$, and the solvent is removed in vacuo to yield the title compound (10 g). $^1$H NMR: δ 2.19 (2×CH$_3$, s), 2.760–2.804 (2×CH$_2$, t), 2.600–2.645 (2×CH$_2$, t), 5.735 (CH$_2$ bridge, s).

PREPARATION 20

Methylene Bis(succinimidylazelate)

1-(3-Dimethylaminopropyl)-3-ethylcarbodiimide hydrochloride (1.49 g, 7.71 mmol) was added in portions to a stirred solution of methylene bis(hydrogen azelate) from Example 25 (1.00 g, 2.57 mmol) and N-hydroxysuccinimide (0.89 g, 7.71 mmol) in dry dimethylformamide at ambient temperature. After 20 hours stirring, the reaction mixture was poured into ice-water and the product precipitated as an oil. The colourless oil was dissolved in diethylether (50 ml), washed with water (3×10 ml) and dried over MgSO$_4$. The solvent was removed under reduced pressure and hexane (5 ml) was added to the oily product. After seven days storage at 4° C. the oil had crystallized to a white, waxy solid. Yield: 1.50 g (69%). m.p.: 45°–47° C. $^{13}$C NMR (75 MHz, CDCl$_3$) δ: 24.42, 24.46, 25.59, 28.48, 28.63, 30.85, 33.82, 79.61, 168.6, 169.30, 172.34.

PREPARATION 21

Methylene Bis(sulphosuccinimidylazelate) Sodium Salt

Methylene bis(hydrogen azelate) (0.38 g, 1 mmol), N-hydroxysuccinimide sodium salt (0.48 g, 2.2 mmol) and dicyclohexylcarbodiimide (0.45 g, 2.2. mmol) were dissolved in dimethylformamide (10 ml). The suspension was stirred overnight at room temperature under an atmosphere of nitrogen. The reaction mixture was filtered and purified by reversed phase chromatography (RP-8) with water/acetonitrile (1:1) as eluant to give the title compound.

PREPARATION 22 a) Methylene bis(10,11-dihydroxyundecanoate)

N-Methylmorpholine-N-oxide (13.5 g, 11 mmol) and methylene bis (10-undecenoate) from Preparation 15(b) (19 g, 5 mmol) were dissolved in 400 ml of a mixture of tetrahydrofuran and water (3:1 v/v). A catalytic amount of osmium tetroxide was added, and the solution stirred at ambient temperature for 20 hours. TLC indicated complete consumption of the starting material. Excess sodium hydrogen sulphite and sodium chloride were then added to the reaction mixture. The product was extracted from the resulting mixture with ethyl acetate (400 ml) and the water phase was washed with ethyl acetate (3×50 ml). The combined organic phases were dried and evaporated, and the product recrystallised from tetrahydrofuran to yield 14.5 g (68%) of the product as a white solid. $^{13}$C NMR (45 MHz) CD$_3$OD: δ 24.6–34.0 (16 ×CH$_2$), 66.6 (2×CH$_2$OH), 72.3 (2×CHOH), 79.2 (O—CH$_2$—O), 174.0 (2×C=O).

b) Methylene bis(10-oxodecanoate)

Methylene bis(10,11-dihydroxyundecanoate) (2.24 g, 5 mmol) was dissolved in 150 ml tetrahydrofuran. Sodium metaperiodate (2.06 g, 10 mmol) was dissolved in 150 ml water and added dropwise to the tetrahydrofuran solution. TLC indicated full consumption of the diol after 60 minutes, whereupon sodium chloride was added to the reaction mixture until the two phases separated. The water phase was extracted with diethyl ether (3×50 ml). The combined organic phases was dried with magnesium sulphate and evaporated to give the title product as an oil, 1.43 g (74%). $^{13}$C NMR (45 MHz) CDCl$_3$: δ 21.9–43.9 (16×CH$_2$), 79.1 (O—CH$_2$—O), 173.0 (2×C=O), 202.6 (2×CHO).

Example 1

1. Gas-filled albumin microspheres (i.e., albumin-encapsulated gas microbubbles) are prepared according to EP-A-0359 246 and resuspended to homogeneity by gentle rolling on a vial roller.

2. 25 ml of the suspension are poured into a 25 ml separating funnel and left for 30 min. The bottom 20 ml are discarded.

3. To the remaining 5 ml is added 20 ml of a phosphate buffer (20 mM NAPO$_4$, pH 7.0), and the resulting suspension is transferred to a vial with a cap septum.

4. The vial is centrifuged upside down at 170×g for 5 min.

5. The solution underneath the microsphere layer is withdrawn using a syringe, and the microspheres are resuspended in 25 ml of the phosphate buffer by 10 min of gentle rolling.

6. Points 4 and 5 are repeated twice.

7. The resulting suspension is centrifuged as in point 4, and the microspheres are resuspended in the phosphate buffer to a final concentration of about 5×10$^8$ particles per ml.

8. The crosslinker methylene bis(α-formylacetate), prepared as described in Preparation 1, is added to the suspension, and the crosslinking reaction is allowed to proceed for the desired time (usually 30–60 min) under gentle rolling.

9. 1.5M Tris-HCl-buffer (pH 8.8) is added to a final concentration of 0.25M, and the suspension is rolled gently for 10 min.

10. The vial is centrifuged as in point 4, and the solution underneath the microsphere layer is removed as in point 5.

11. The microspheres are resuspended in phosphate buffer (same volume as final volume in point 9), and the suspension is rolled for 10 min.

12. Points 10 and 11 are repeated twice.

13. The resulting suspension is centrifuged as in point 4, and the microspheres are resuspended in the phosphate buffer to a final concentration of about 5×10$^8$ particles per ml.

14. This final suspension of crosslinked gas/albumin microspheres is stored at 4° C.

Example 2–22

The procedure of Example 1 is repeated using crosslinking agents prepared as described in Preparations 2–22, except that dimethyl sulphoxide is used in place of phosphate buffer in the processing of the gas-filled albumin microspheres according to steps 3–7 and the crosslinking agent is added in step 8 as a solution in dimethyl sulphoxide.

The number and size distribution of the products are determined by Coulter counter analysis.

We claim:

1. Microbubbles comprising a protein capable of formation of gas-containing microbubbles, said microbubbles containing gas comprising sulphur hexafluoride or a low molecular weight fluorinated hydrocarbon.

2. Microbubbles as claimed in claim 1 wherein said hydrocarbon is perfluorinated.

3. Microbubbles as claimed in claim 1 wherein said protein is albumin, gelatin or y-globulin.

4. Microbubbles as claimed in claim 3 wherein said protein is human serum albumin.

5. An aqueous dispersion comprising microbubbles as claimed in claim 1.

6. An aqueous dispersion comprising microbubbles as claimed in claim 2.

7. An aqueous dispersion comprising microbubbles as claimed in claim 3.

8. An aqueous dispersion comprising microbubbles as claimed in claim 4.

9. Microbubbles as claimed in claim 1 wherein said protein is crosslinked with crosslinking groups containing biodegradable linkages.

10. Microbubbles as claimed in claim 9 wherein the crosslinking groupings contain biodegradable linkages selected from the group consisting of amide, imide, imine, ester, anhydride, acetal, carbamate, carbonate, carbonate ester and disulphide groups.

11. Microbubbles as claimed in claim 10 wherein the crosslinking groups contain biodegradable linkages of formula

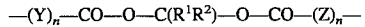

$$-(Y)_n-CO-O-C(R^1R^2)-O-CO-(Z)_n-$$

where Y and Z, which may be the same or different, are —O—, —S— or —NR$^3$; R$^1$ and R$^2$, which may be the same or different, are hydrogen atoms or carbon-attached monovalent organic groups or together represent a carbon-attached divalent organic group; R$^3$ is a hydrogen atom or an organic group; and the symbols n, which may be the same or different, are zero or 1.

12. Microbubbles as claimed in claim 1 having an average size of 0.1–10 μm.

13. Microbubbles as claimed in claim 12 having an average size of 1–7 μm.

14. Microbubbles as claimed in claim 9 having an average size of 0.1–10 μm.

15. Microbubbles as claimed in claim 14 having an average size of 1–7 μm.

16. An aqueous dispersion comprising microbubbles as claimed in claim 9.

17. A diagnostic ultrasound contrast agent comprising microbubbles as claimed in claim 9.

18. A contrast agent as claimed in claim 17 having a half-life in vivo of not more than 48 hours.

19. A contrast agent as claimed in claim 17 wherein said microbubbles are dispersed in an aqueous carrier.

20. A process for the preparation of a contrast agent which comprises generating microbubbles comprising a protein capable of formation of gas-containing microbubbles, said microbubbles containing gas comprising sulphur hexafluoride or a low molecular weight fluorinated hydrocarbon.

21. A process as claimed in claim 20 which comprises shaking or sonicating a protein-containing mixture in the presence of sulphur hexafluoride or a low molecular weight fluorinated hydrocarbon to generate a fluid dispersion of said microbubbles.

22. A process as claimed in claim 21 wherein said protein-containing mixture comprises protein in an aqueous medium.

23. A process as claimed in claim 21 wherein said hydrocarbon is perfluorinated.

24. A process for the preparation of a contrast agent which comprises crosslinking, microbubbles comprising a protein capable of formation of gas-containing microbubbles, said microbubbles containing gas comprising sulphur hexafluoride or a low molecular weight fluorinated hydrocarbon, and said crosslinking introducing crosslinking groups which contain biodegradable linkages.

25. A process as claimed in claim 24 wherein crosslinking is effected using a crosslinking agent of formula (I)

$$A^1{-}X{-}A^2 \qquad (I)$$

where X is a linking group containing one or more biodegradable linkages selected from the group consisting of amide, imide, imine, ester, anhydride, acetal, carbamate, carbonate, carbonate ester and disulphide groups; and $A^1$ and $A^2$, which may be the same or different, are functional groups reactive with proteins.

26. A process as claimed in claim 24 wherein crosslinking is effected using a crosslinking agent of formula (I)

$$A^1{-}X{-}A^2 \qquad (I)$$

where X is a linking group containing one or more biodegradable linkages of formula $$-(Y)_n{-}CO{-}O{-}C(R^1R^2){-}O{-}CO{-}(Z)_n-$$

where Y and Z, which may be the same or different, are —O—, —S— or —NR³; $R^1$ and $R^2$, which may be the same or different, are hydrogen atoms or carbon-attached monovalent organic groups or together represent a carbon-attached divalent organic group; $R^3$ is a hydrogen atom or an organic group; and the symbols n, which may be the same or different, are zero or 1; and $A^1$ and $A^2$, which may be the same or different, are functional groups reactive with proteins.

27. A process as claimed in claim 25 in which $A^1$ and $A^2$ are both aldehyde groups.

28. A process as claimed in claim 26 in which $A^1$ and $A^2$ are both aldehyde groups.

29. A process as claimed in claim 24 wherein said hydrocarbon is perfluorinated.

30. A method of enhancing ultrasound images of a vascular system comprising administering to said system a diagnostic ultrasound contrast agent according to claim 17.

* * * * *

(12) REEXAMINATION CERTIFICATE (4586th)
United States Patent
Klaveness et al.

(10) Number: US 5,529,766 C1
(45) Certificate Issued: Jun. 4, 2002

(54) CONTRAST AGENTS

(75) Inventors: Jo Klaveness, Oslo; Pål Rongved, Nesoddtaugen; Per Strande, Oslo, all of (NO)

(73) Assignee: Nycomed Imaging AS, Oslo (NO)

Reexamination Request:
No. 90/004,712, Jul. 31, 1997

Reexamination Certificate for:
| | |
|---|---|
| Patent No.: | 5,529,766 |
| Issued: | Jun. 25, 1996 |
| Appl. No.: | 08/119,218 |
| Filed: | Oct. 29, 1993 |

(22) PCT Filed: Mar. 28, 1992

(86) PCT No.: PCT/EP92/00716
§ 371 (c)(1),
(2), (4) Date: Oct. 29, 1993

(87) PCT Pub. No.: WO92/17213
PCT Pub. Date: Oct. 15, 1992

(30) Foreign Application Priority Data

Mar. 28, 1991 (GB) .............................................. 9106686

(51) Int. Cl.$^7$ ............................................. A61K 49/00
(52) U.S. Cl. ..................................................... 424/9.52
(58) Field of Search ............................... 424/9.51, 9.52; 128/662.02

(56) References Cited

U.S. PATENT DOCUMENTS

| | | | |
|---|---|---|---|
| 4,265,251 A | 5/1981 | Tickner | 128/660 |
| 4,276,885 A | 7/1981 | Tickner et al. | 128/600 |
| 4,718,433 A | 1/1988 | Feinstein | 424/9.52 |
| 4,774,958 A | 10/1988 | Feinstein | 128/660.01 |
| 4,832,941 A | 5/1989 | Berwing et al. | |
| 4,844,882 A | 7/1989 | Widder et al. | 424/660.01 |
| 4,957,656 A | 9/1990 | Cerny | 252/311 |
| 5,147,631 A | 9/1992 | Glajch | 424/9.52 |
| 5,413,774 A | 5/1995 | Schneider | 424/9.51 |
| 5,425,366 A | 6/1995 | Reinhardt | 600/458 |
| 5,501,863 A | 3/1996 | Rössling et al. | 424/489 |
| 5,527,521 A | 6/1996 | Unger | 424/9.3 |
| 5,547,656 A | 8/1996 | Unger | 424/9.4 |
| 5,558,094 A | 9/1996 | Quay | 600/458 |
| 5,573,751 A | 11/1996 | Quay | 424/9.52 |
| 5,578,292 A | 11/1996 | Schneider | 424/9.51 |
| 5,705,187 A | 1/1998 | Unger | 424/450 |
| 5,711,933 A | 1/1998 | Bichon | 424/9.52 |

FOREIGN PATENT DOCUMENTS

| | | |
|---|---|---|
| AU | 40651/89 | 3/1990 |
| CA | A1 2036107 | 8/1991 |
| EP | 0 224 934 | 6/1987 |
| EP | 0 324 938 | 7/1989 |
| EP | 0 359 246 | 3/1990 |
| EP | 0 441 468 A2 | 8/1991 |
| EP | 0 458 745 A1 | 11/1991 |
| WO | WO 90/01952 | 3/1990 |
| WO | WO 91/12823 | 9/1991 |
| WO | WO 92/05806 | 4/1992 |
| WO | 95/01187 | 1/1995 |

OTHER PUBLICATIONS

J. M. Peeters, et al. Comparison of four bifunctional reagents for coupling peptides to proteins and the effect of the three moities on the immunogenicity of the conjugates, Journal of Immunological Methods, vol. 120 (1989) pp. 133–143.

H.J. Bleeker et al. Ultrasonic characterization of Albunex®, a new contrast agent, J. Acoust. Soc. Am. 87 (4), Apr. 1990, pp. 1792–1797.

Halldis Hellebust et al., Biochemical charaterization of air–filled albumin microspheres, Biotechnol. Appl. Biochem, 18 (1993), pp. 227–237.

C. M. Vygantas et al. "Octafluorcyclobutane and Other Gases for Vitreous Replacement" Arch Ophtalmol, vol. 90, Sep. 1973, p. 235–236.

H. Lincoff, et al. "Intravitreal Disappearance Rates of Four Perfluorocarbon Gases," Arch Opthalmol, vol. 102, Jun. 1984, pp. 928–929.

Ziskin, et al. "Contrast Agents for Diagnostic Ultrasound" Invest. Radiol., vol. 7, pp. 500–505 (1972).

Swanson et al, "Enhancement Agents for Ultrasound: Fundamentals," *Pharmaceuticals in Medical Imaging*, pp. 682–687.

Lincoff et al, "The Perfluorocarbon Gases in the Treatment of Retinal Detachment," *American Academy of Ophthalmology*, pp. 546–551.

Lincoff et al., "Perfluoro–n–Butane," Arch Ophthalmol (Mar. 1983) 101: 460–462.

Jacobs, "Intracular Gas Measurement Using A–Scan Ultrasound," *Current Eye Research* (1986) 5:575–578.

Lincoff et al., "Intravitreal Expansion of Perfluorocarbon Bubbles," Arch Ophthalamol (Sep. 1980) 98: 1646.

Lincoff et al., "Intravitreal Longevity of Three Perfluorocarbon Gases," Arch Ophthalmol (Sep. 1980) 98: 1610–1611.

Gardner et al., "A Survey of Intraocular Gas Use in North America," Arch Ophthalmol (Sep. 1988) 106: 1188–1189.

Feinstein, "Myocardial Persusion Imaging: Contrast Echocardiography Today and Tomorrow," *JACC* (Jul. 1986) 8:251–253.

Dupont Technical Bulletin, "Freon:Technical Bulletin," *Du Pont Technical Bulletin* (1964) pp. 1–8.

Dupont, "Freon Fluorocarbons Properties and Applications," *Dupont Technical Bulletin* (1987) pp. 1–10.

Miller et al., "Physicochemical Approaches to the Mode of Action of General Anesthetics," *Anesthesiology* (Apr. 1972) 36:339–351.

(List continued on next page.)

*Primary Examiner*—Michael G. Hartley

(57) ABSTRACT

The invention relates to ultrasound contrast agents comprising vesicles comprising a protein capable of formation of gas-containing vesicles, wherein the vesicles contain gas which comprises sulphur hexafluoride or a low molecular weight fluorinated hydrocarbon. These contrast agents exhibit stability in vivo upon administration so as to permit ultrasound visualization while allowing rapid subsequent elimination from the system.

OTHER PUBLICATIONS

Pietersen, "A New Warning System for Fires of Electrical Origin," *CERN* (Mar. 7, 1977) pp. 1–5.

Keller et al., "The Behavior of Sonicated Albumin Microbubbles Within the Microcirculation: A Basis for Their Use During Myocardial Contrast Echocardiography," *Circulation Res.* (Aug. 1989) 65(2):458–467.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–30 is confirmed.

\* \* \* \* \*